US012686669B2

(12) United States Patent
Yu et al.

(10) Patent No.: US 12,686,669 B2
(45) Date of Patent: ***Jul. 21, 2026

(54) METHOD FOR SEPARATING AND PURIFYING TETRAHYDROCANNABIVARIN BY MEANS OF HIGH-SPEED COUNTERCURRENT CHROMATOGRAPHY

(71) Applicant: Shanghai Tauto Biotech Co., Ltd., Shanghai (CN)

(72) Inventors: Qi Yu, Shanghai (CN); Li Deng, Shanghai (CN)

(73) Assignee: Shanghai Tauto Biotech Co., Ltd., Shanghai (CN)

( * ) Notice: Subject to any disclaimer, the term of this patent is extended or adjusted under 35 U.S.C. 154(b) by 356 days.

This patent is subject to a terminal disclaimer.

(21) Appl. No.: 18/285,388

(22) PCT Filed: Mar. 31, 2022

(86) PCT No.: PCT/CN2022/084449
§ 371 (c)(1),
(2) Date: Oct. 3, 2023

(87) PCT Pub. No.: WO2022/213880
PCT Pub. Date: Oct. 13, 2022

(65) Prior Publication Data
US 2024/0182437 A1     Jun. 6, 2024

(30) Foreign Application Priority Data

Apr. 7, 2021    (CN) .......................... 202110372479.1

(51) Int. Cl.
*C07D 311/80*         (2006.01)

(52) U.S. Cl.
CPC .................................. *C07D 311/80* (2013.01)

(58) Field of Classification Search
CPC ...... C07D 311/80; G01N 30/26; G01N 30/50; G01N 30/88; G01N 30/00; B01D 15/1892; B01D 15/00; B01D 11/0492; B01D 17/038; A61K 31/352; A61P 1/18; A61P 3/10

USPC .......................................................... 210/635
See application file for complete search history.

(56) References Cited

U.S. PATENT DOCUMENTS

| | | | | |
|---|---|---|---|---|
| 2018/0036278 A1* | 2/2018 | Rutz | .................... | A61K 31/658 |
| 2018/0162828 A1* | 6/2018 | Nadal Roura | ..... | B01D 11/0492 |

FOREIGN PATENT DOCUMENTS

| | | | | |
|---|---|---|---|---|
| CN | 109942380 | 6/2019 | | |
| CN | 111788171 | 10/2020 | | |
| CN | 113135885 | 7/2021 | | |
| WO | WO-2019145552 A1 * | 8/2019 | ......... | B01D 11/0492 |
| WO | 2020180759 | 9/2020 | | |
| WO | WO 2020/180759 A1 * | 9/2020 | .......... | B01D 17/038 |

OTHER PUBLICATIONS

"International Search Report (Form PCT/ISA/210) of PCT/CN2022/084449," mailed on Jun. 22, 2022, with English translation thereof, pp. 1-4.

* cited by examiner

*Primary Examiner* — Akash K Varma

(74) *Attorney, Agent, or Firm* — JCIPRNET

(57) ABSTRACT

The present invention relates to a method for separating and purifying tetrahydrocannabivarin (THCV) by means of high-speed countercurrent chromatography, the method comprising: sufficiently shaking a solvent system, leaving same to stand, and separately collecting upper and lower phases; dissolving full-spectrum refined hemp oil in the upper phase, taking the upper phase as a stationary phase and the lower phase as a mobile phase, performing separation by using high-speed countercurrent chromatography to obtain a mixed solution of tetrahydrocannabivarin and the mobile phase, and removing the mobile phase to obtain the tetrahydrocannabivarin. According to the present invention, THCV with a purity of >95% is obtained by separation and purification from full-spectrum refined hemp oil by using high-speed countercurrent chromatography technology for the first time.

4 Claims, No Drawings

METHOD FOR SEPARATING AND PURIFYING TETRAHYDROCANNABIVARIN BY MEANS OF HIGH-SPEED COUNTERCURRENT CHROMATOGRAPHY

CROSS-REFERENCE TO RELATED APPLICATION

This application is a 371 of international application of PCT application serial no. PCT/CN2022/084449, filed on Mar. 31, 2022, which claims the priority benefit of China application no. 202110372479.1, filed on Apr. 7, 2021. The entirety of each of the above mentioned patent applications is hereby incorporated by reference herein and made a part of this specification.

BACKGROUND

Technical Field

The present invention belongs to the field of treatment of cannabinols, and particularly relates to a method for separating and purifying tetrahydrocannabivarin by means of high-speed countercurrent chromatography.

Description of Related Art

Tetrahydrocannabivarin (THCV) has a molecular formula of $C_{19}H_{26}O_2$, and exists in industrial hemp. Generally, a preparation method is obtaining an extract containing tetrahydrocannabivarin by performing alcohol extraction and the like on industrial hemp. The THCV may be used for protecting islet cells and the like at present.

A high-speed counter-current chromatography (HSCCC) technology is a novel separation and purification technology based on a liquid-liquid distribution principle, which does not need any solid support or carrier, a stationary phase and a mobile phase are both liquid, and irreversible adsorption is absent. At present, there is no related technology for separating tetrahydrocannabivarin by utilizing the high-speed counter-current chromatography disclosed.

SUMMARY

The technical problem to be solved by the present invention is to provide a method for separating and purifying tetrahydrocannabivarin by means of high-speed countercurrent chromatography, and the tetrahydrocannabivarin with a purity >95% is obtained through one-step separation and purification by a solvent system.

The present invention provides a method for separating and purifying tetrahydrocannabivarin by means of high-speed countercurrent chromatography, including:

sufficiently shaking a solvent system, carrying out standing, and separately collecting an upper phase and a lower phase; and dissolving industrial hemp full-spectrum refined oil in the upper phase, performing separation by adopting high-speed counter-current chromatography with the upper phase as a stationary phase and the lower phase as a mobile phase to obtain mixed liquor of tetrahydrocannabivarin and the mobile phase, and removing the mobile phase to obtain the tetrahydrocannabivarin; wherein the solvent system is obtained by mixing n-hexane or n-heptane, ethyl acetate, methanol or ethanol and water according to a volume ratio of (4-8):(0-2):(3-7):(1-3).

Ultrasonic degassing treatment is performed on the upper phase and the lower phase obtained by separate collection.

Conditions of high-speed counter-current chromatography are: a rotating direction is forward rotation with a rotating speed of 800 rpm; a column temperature is 25° C.; a flow rate of the mobile phase is 5 mL/min; and a detection wavelength of a detector is 214 nm.

Process conditions for removing the mobile phase are: rotary evaporation vacuum drying is performed under the conditions of 55° C. and −0.085 MPa.

Beneficial Effects (1) In the present invention, the tetrahydrocannabivarin with the purity >95% is obtained from the industrial hemp full-spectrum refined oil through separation and purification by utilizing a high-speed counter-current chromatography technology the first time, and the difference from separating other cannabinol components is that: the different solvent system is adopted, and ethyl acetate and the like are added to achieve the better separation effect for the tetrahydrocannabivarin and other cannabinol components.

(2) The high-speed counter-current chromatography technology in the present invention has the advantages of no sample loss, no pollution, high efficiency and the like, and has good market application prospects.

DESCRIPTION OF THE EMBODIMENTS

The present invention is further described below in combination with specific embodiments. It should be understood that these embodiments are merely used for illustrating the present invention, instead of limiting the scope of the present invention. In addition, it should be understood that after reading the content taught in the present invention, those skilled in the art can make various modifications or changes to the present invention, and these equivalent forms also fall within the scope of the claims attached to this application.

Reagents and instruments adopted in the embodiments are as follows:

Reagents: n-hexane, n-heptane, methanol, ethanol and ethyl acetate are all analytic reagents produced by the Sinopharm Chemical Reagent Co., Ltd., water is deionized water, and industrial hemp full-spectrum refined oil is a commercially available product.

Instruments: a high-speed counter-current chromatograph is a TBE-300C high-speed counter-current chromatograph produced by the Shanghai Tauto Biotech Co., Ltd.

Embodiment 1

N-hexane, methanol and water were mixed according to a volume ratio of 5:5:2.5 to obtain a solvent system, the solvent system was added into a separatory funnel, sufficiently shaken and subjected to standing for phase splitting so as to obtain two-phase mixed liquor, and an upper phase and a lower phase were separately collected and placed into an ultrasonic oscillator for ultrasonic degassing treatment. Industrial hemp full-spectrum refined oil was dissolved in the upper phase, and then, with the upper phase as a stationary phase and the lower phase as a mobile phase, separation was carried out by adopting high-speed counter-current chromatography, wherein chromatography conditions are set as: forward rotation with a rotating speed of 800 rpm; a column temperature of 25° C.; a flow rate of the mobile phase of 5 mL/min; and a detection wavelength of a detector of 214 nm; and with completion of sample injection being 0 min. mixed liquor of tetrahydrocannabivarin (THCV) and the mobile phase was obtained at 80-90 min. the mixed liquor was placed in a rotary evaporator to be subjected to rotary evaporation vacuum drying under the conditions of a bath temperature of 55° C. and vacuum pressure of –0.085 MPa. and the lower phase was removed to obtain a THCV product.

By analyzing the purity of the product obtained in the present embodiment through HPLC, results showed that: the purity of the THCV was 89.04%.

Embodiment 2

N-hexane, ethyl acetate, methanol and water were mixed according to a volume ratio of 5:1:5:1.5 to obtain a solvent system, the solvent system was added into a separatory funnel, sufficiently shaken and subjected to standing for phase splitting so as to obtain two-phase mixed liquor, and an upper phase and a lower phase were separately collected and placed into an ultrasonic oscillator for ultrasonic degassing treatment. Industrial hemp full-spectrum refined oil was dissolved in the upper phase, and then, with the upper phase as a stationary phase and the lower phase as a mobile phase, separation was carried out by adopting high-speed countercurrent chromatography, wherein chromatography conditions are set as: forward rotation with a rotating speed of 800 rpm; a column temperature of 25° C.; a flow rate of the mobile phase of 5 mL/min; and a detection wavelength of a detector of 214 nm; and with completion of sample injection being 0 min, mixed liquor of tetrahydrocannabivarin (THCV) and the mobile phase was obtained at 110-120 min, the mixed liquor was placed in a rotary evaporator to be subjected to rotary evaporation vacuum drying under the conditions of a bath temperature of 55° C. and vacuum pressure of –0.085 MPa, and the lower phase was removed to obtain a THCV product.

By analyzing the purity of the product obtained in the present embodiment through HPLC, results showed that: the purity of the THCV was 95.82%.

Embodiment 3

N-heptane, ethyl acetate, ethanol and water were mixed according to a volume ratio of 6:0.5:6:2 to obtain a solvent system, the solvent system was added into a separatory funnel, sufficiently shaken and subjected to standing for phase splitting so as to obtain two-phase mixed liquor, and an upper phase and a lower phase were separately collected and placed into an ultrasonic oscillator for ultrasonic degassing treatment. Industrial hemp full-spectrum refined oil was dissolved in the upper phase, and then, with the upper phase as a stationary phase and the lower phase as a mobile phase, separation was carried out by adopting high-speed countercurrent chromatography, wherein chromatography conditions are set as: forward rotation with a rotating speed of 800 rpm; a column temperature of 25° C.; a flow rate of the mobile phase of 5 mL/min; and a detection wavelength of a detector of 214 nm; and with completion of sample injection being 0 min, mixed liquor of tetrahydrocannabivarin (THCV) and the lower phase was obtained at 90-100 min, the mixed liquor was placed in a rotary evaporator to be subjected to rotary evaporation vacuum drying under the conditions of a bath temperature of 55° C. and vacuum pressure of –0.085 MPa, and the lower phase was removed to obtain a THCV product.

By analyzing the purity of the product obtained in the present embodiment through HPLC, results showed that: the purity of the THCV was 95.37%.

What is claimed is:

1. A method for separating and purifying tetrahydrocannabivarin by means of high-speed countercurrent chromatography, comprising:
   sufficiently shaking a solvent system, subjecting the solvent system to standing for phase splitting so as to obtain two-phase mixed liquor, and obtaining an upper phase and a lower phase by a separate collection; and
   dissolving an industrial hemp full-spectrum refined oil in the upper phase, performing a separation by adopting the high-speed countercurrent chromatography with the upper phase as a stationary phase and the lower phase as a mobile phase to obtain a mixed liquor of the tetrahydrocannabivarin and the mobile phase, and removing the mobile phase to obtain the tetrahydrocannabivarin; wherein; the solvent system is obtained by mixing N-hexane, ethyl acetate, methanol and water according to a volume ratio of 5:1:5:1.5 or by mixing N-heptane, ethyl acetate, ethanol and water according to a volume ratio of 6:0.5:6:2.

2. The method according to claim 1, wherein an ultrasonic degassing treatment is performed on the upper phase and the lower phase obtained by the separate collection.

3. The method according to claim 1, wherein conditions of the high-speed countercurrent chromatography are: a rotating direction is forward rotation with a rotating speed of 800 rpm; a column temperature is 25° C.; a flow rate of the mobile phase is 5 mL/min; and a detection wavelength of a detector is 214 nm.

4. The method according to claim 1, wherein process conditions for removing the mobile phase are: a rotary evaporation vacuum drying is performed under conditions of 55° C. and –0.085 MPa.

* * * * *